(12) United States Patent
Aylsworth et al.

(10) Patent No.: US 7,459,008 B2
(45) Date of Patent: Dec. 2, 2008

(54) METHOD AND SYSTEM OF OPERATING A TRANS-FILL DEVICE

(76) Inventors: Alonzo C. Aylsworth, 19359 Ossenfort Ct., Wildwood, MO (US) 63038; Charles R. Aylsworth, 19359 Ossenfort Ct., Wildwood, MO (US) 63038; Kevin G. McCulloh, 425 Canyon Crest Dr., Simi Valley, CA (US) 93065

( * ) Notice: Subject to any disclaimer, the term of this patent is extended or adjusted under 35 U.S.C. 154(b) by 441 days.

(21) Appl. No.: 11/377,065

(22) Filed: Mar. 16, 2006

(65) Prior Publication Data
US 2007/0214960 A1  Sep. 20, 2007

(51) Int. Cl.
*A61M 16/00* (2006.01)
*A62B 7/00* (2006.01)

(52) U.S. Cl. ............... 95/8; 95/19; 95/130; 96/111; 96/113; 96/116; 128/204.21; 128/205.18; 128/205.24

(58) Field of Classification Search ............ 95/95–106, 95/8, 29, 33, 130; 96/111, 113, 114, 116, 96/121–133; 128/204.18, 204.21, 205.12, 128/205.18, 205.24, 205.27; 141/18
See application file for complete search history.

(56) References Cited

U.S. PATENT DOCUMENTS

| | | | |
|---|---|---|---|
| 2,160,326 A | 5/1939 | Carbonara |
| 2,469,434 A | 5/1949 | Hansen et al. |
| 4,428,372 A | 1/1984 | Beysel et al. |
| 4,449,990 A | 5/1984 | Tedford, Jr. |
| 4,561,287 A | 12/1985 | Rowland |
| 4,587,967 A | 5/1986 | Chu et al. |
| 4,612,928 A | 9/1986 | Tiep et al. |
| 4,627,860 A | 12/1986 | Rowland |
| 4,673,415 A | 6/1987 | Stanford |
| 4,765,804 A | 8/1988 | Lloyd-Williams et al. |
| 4,838,261 A | 6/1989 | von dem Hagen |
| 4,860,803 A | 8/1989 | Wells |
| 4,869,733 A | 9/1989 | Stanford |
| 5,060,514 A | 10/1991 | Aylsworth |
| 5,071,453 A | 12/1991 | Hradek et al. |
| 5,078,757 A | 1/1992 | Rottner et al. |
| 5,144,945 A | 9/1992 | Nishino et al. |
| 5,195,874 A | 3/1993 | Odagiri |
| 5,199,423 A | 4/1993 | Harral et al. |
| 5,248,320 A | 9/1993 | Garrett et al. |
| 5,313,820 A | 5/1994 | Aylsworth |
| 5,354,361 A | 10/1994 | Coffield |
| 5,369,979 A | 12/1994 | Aylsworth et al. |
| 5,405,249 A | 4/1995 | Benson |
| 5,452,621 A | 9/1995 | Aylsworth et al. |

(Continued)

OTHER PUBLICATIONS

PCT International Search Report, PCT/US2007/063127 dated Oct. 5, 2007, 2pp.

*Primary Examiner*—Frank M Lawrence
(74) *Attorney, Agent, or Firm*—Michael W. Haas

(57) ABSTRACT

A method and system of operating a trans-fill device. At least some of the illustrative embodiments are methods comprising generating an enriched gas stream from atmospheric air, and operating an intensifier which, when provided the enriched gas stream, produces a cylinder fill gas stream. The operating continues in the absence of the enriched gas stream being provided to the intensifier.

25 Claims, 3 Drawing Sheets

U.S. PATENT DOCUMENTS

| | | |
|---|---|---|
| 5,474,595 A | 12/1995 | McCombs |
| 5,584,669 A | 12/1996 | Becker |
| 5,593,291 A | 1/1997 | Lynn |
| 5,603,315 A | 2/1997 | Sasso, Jr. |
| 5,709,203 A | 1/1998 | Gier |
| 5,746,806 A | 5/1998 | Aylsworth et al. |
| 5,858,062 A | 1/1999 | McCulloh et al. |
| 5,915,834 A | 6/1999 | McCulloh |
| 5,918,596 A | 7/1999 | Heinonen |
| 5,979,440 A | 11/1999 | Honkonen et al. |
| 5,988,165 A | 11/1999 | Richey, II et al. |
| 6,131,572 A | 10/2000 | Heinonen |
| 6,152,192 A | 11/2000 | Klotz et al. |
| 6,263,927 B1 | 7/2001 | Carroll |
| 6,302,107 B1 | 10/2001 | Richey, II et al. |
| 6,334,468 B1 | 1/2002 | Friestad |
| 6,342,090 B1 | 1/2002 | Cao |
| 6,346,139 B1 | 2/2002 | Czabala |
| 6,393,802 B1 | 5/2002 | Bowser et al. |
| 6,394,088 B1 | 5/2002 | Frye et al. |
| 6,446,630 B1 | 9/2002 | Todd, Jr. |
| 6,478,857 B2 | 11/2002 | Czabala |
| 6,629,525 B2 | 10/2003 | Hill et al. |
| 6,651,653 B1 | 11/2003 | Honkonen et al. |
| 6,681,764 B1 | 1/2004 | Honkonen et al. |
| 6,698,423 B1 | 3/2004 | Honkonen et al. |
| 6,701,923 B2 | 3/2004 | Cazenave et al. |
| 2004/0079359 A1 | 4/2004 | Aylsworth et al. |
| 2007/0084342 A1* | 4/2007 | Hunter et al. ............. 95/130 |

* cited by examiner

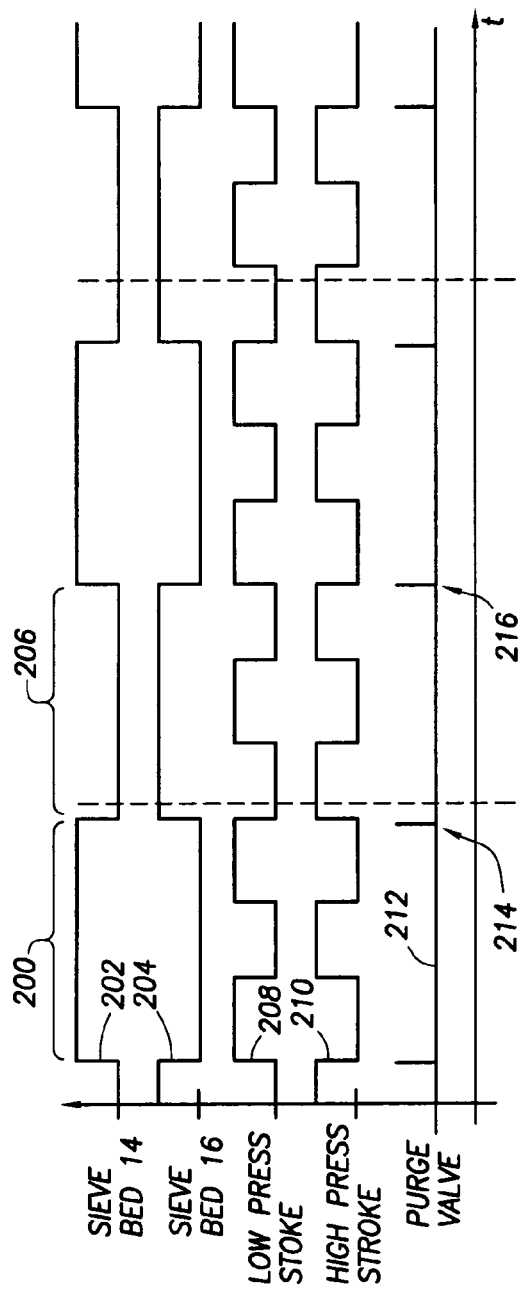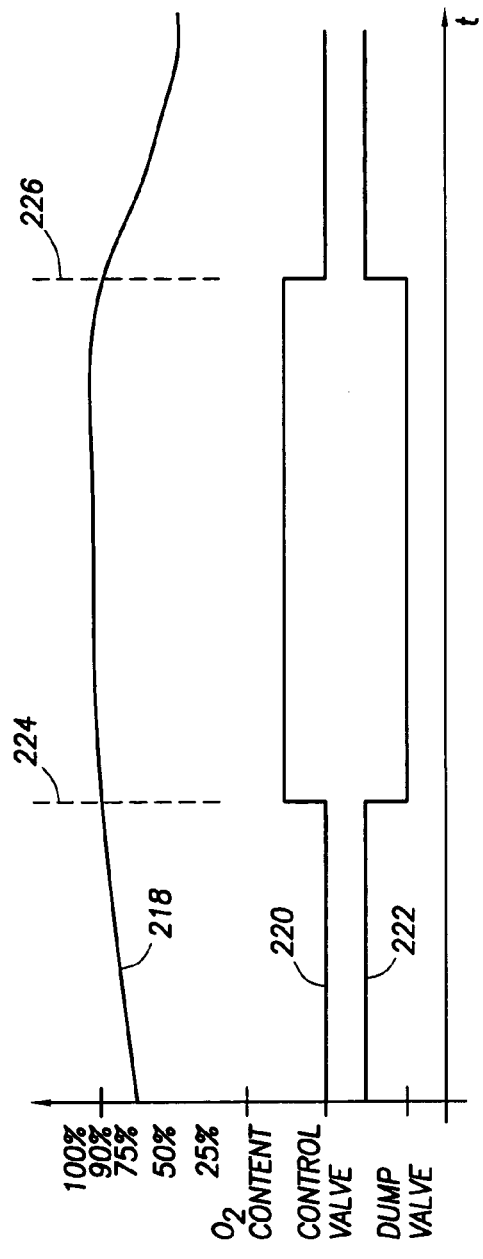

METHOD AND SYSTEM OF OPERATING A TRANS-FILL DEVICE

CROSS-REFERENCE TO RELATED APPLICATIONS

None.

STATEMENT REGARDING FEDERALLY SPONSORED RESEARCH OR DEVELOPMENT

Not applicable.

BACKGROUND

Many patients with lung and/or cardiovascular problems may be required to breathe therapeutic gas in order to obtain sufficient dissolved oxygen in their blood stream. So that these patients may be ambulatory, therapeutic gas may be delivered from a portable cylinder. A portable cylinder may, however, provide only limited volume, and therefore periodically needs to be refilled. While it is possible to have these cylinders exchanged or refilled by way of commercial home health care services, some patients have systems within their homes which generate therapeutic gas and fill portable cylinders with the therapeutic gas. Systems such as these have come to be known as transfer-fill or "trans-fill" systems. However, the trans-fill systems of the related art fill the portable cylinders very slowly, and are prohibitively expensive for most patients.

SUMMARY

The problems noted above are solved in large part by a method and system of operating a trans-fill device. At least some of the illustrative embodiments are methods comprising generating an enriched gas stream from atmospheric air, and operating an intensifier which, when provided the enriched gas stream, produces a cylinder fill gas stream. The operating continues in the absence of the enriched gas stream being provided to the intensifier.

Other illustrative embodiments are systems comprising a compressor, a concentrator fluidly coupled to the compressor (the concentrator creates an enriched gas stream), an intensifier with a motive portion and a compression portion (the motive portion fluidly coupled to the compressor, and the compression portion fluidly coupled to the enriched gas stream on one side and configured to couple to a portable gas cylinder on a second side, wherein the compression portion compresses the enriched gas stream to create a high pressure enriched gas stream), and a control valve fluidly coupled between the concentrator and the intensifier (the valve selectively blocks enriched gas flow to the intensifier). The motive portion of the intensifier continues to draw compressed air from the compressor when the control valve blocks enriched gas flow to the compression portion of the intensifier.

The disclosed devices and methods comprise a combination of features and advantages which enable it to overcome the deficiencies of the prior art devices. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the preferred embodiments of the invention, reference will now be made to the accompanying drawings in which:

FIG. 2A illustrates a timing diagram in accordance with the embodiments of the invention;

FIG. 2B illustrates a timing diagram in accordance with the embodiments of the invention.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct connection. Thus, if a first device couples to a second device, that connection may be through a direct connection, or through an indirect connection via other devices and connections.

Further, when describing "pressure" in this specification, and in the claims, the pressure reference shall be to gauge pressure rather than absolute pressure.

DETAILED DESCRIPTION OF THE PREFERRED EMBODIMENTS

Figure 1:
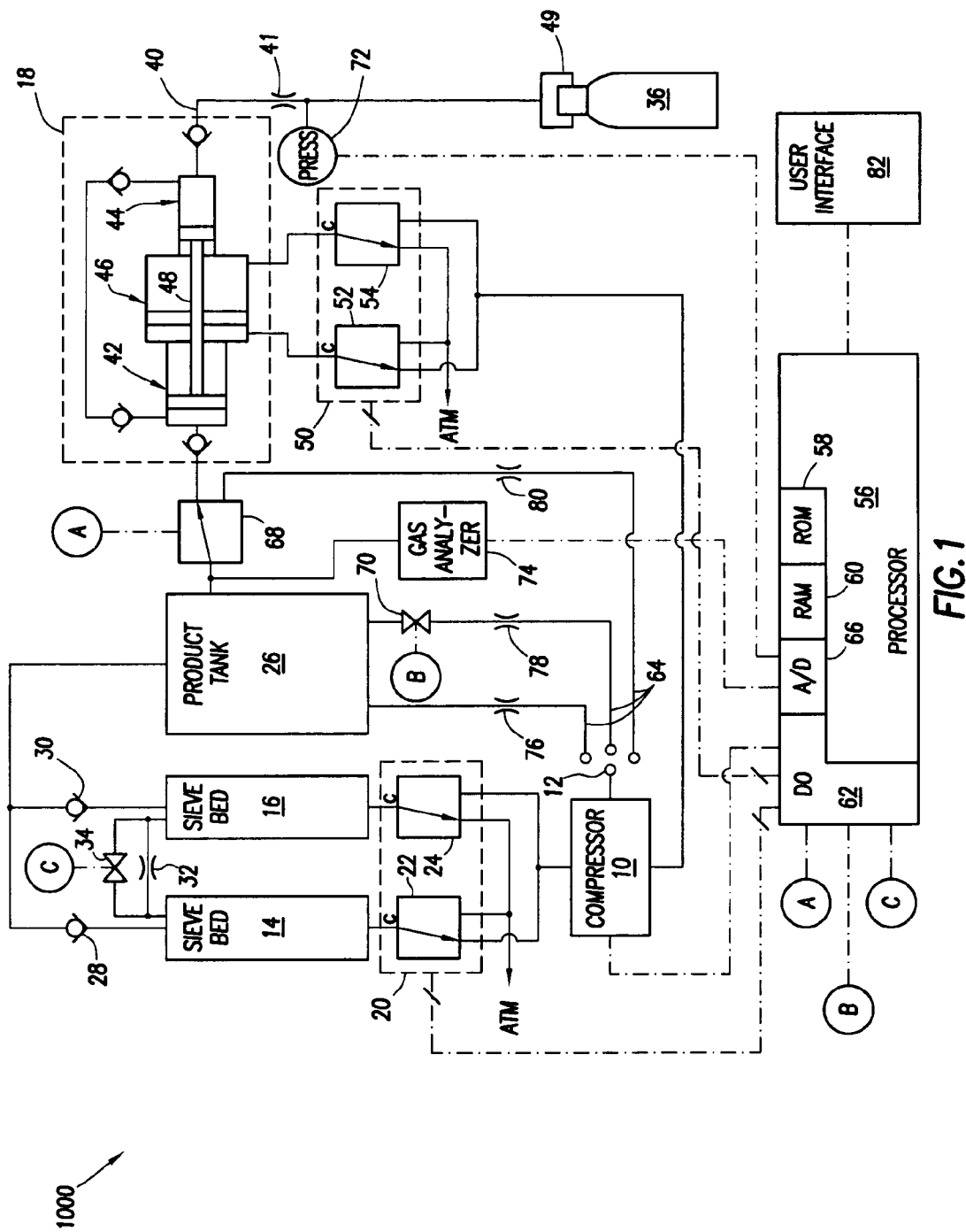
FIG. 1 illustrates a trans-fill system in accordance with the embodiments of the invention.

FIG. 1 illustrates a trans-fill system 1000 for filling portable cylinders in accordance with embodiments of the invention. Devices such as illustrated in FIG. 1 may be used, for example, in a patient's home to fill portable oxygen cylinders for ambulatory use. Trans-fill systems in accordance with embodiments of the invention comprise both electrical components and mechanical components. In order to differentiate between electrical connections and fluid connections, FIG. 1 illustrates electrical connections between devices with dash-dot-dash lines, and fluid connection, (e.g. tubing connections between devices), with solid lines.

FIG. 1 illustrates that a trans-fill system 1000 in accordance with embodiments of the invention comprise a compressor 10. Compressor 10 draws air through inlet 12, compresses the air (in some embodiments to approximately 30 PSI), and provides the air to other devices of the trans-fill system 1000, particularly the sieve beds 14 and 16 and the intensifier 18. In accordance with at least some embodiments, compressor 10 is an electric motor driven compressor having model number 2680CE56-XXX available from Thomas Compressor (A Gardner Denver Product) of Quincy Ill.

Sieve beds 14 and 16 form at least a part of an oxygen concentrator, and in particular a pressure swing absorption (PSA) system. Each sieve bed 14 and 16 is a vessel that is filled in whole or in part with a molecular sieve material, such as OXY-SIEVE 5 available from UOP, LLC of Chicago Ill. In accordance with some embodiments, each of sieve bed 14 and 16 hold approximately 1.5 pounds of molecular sieve material, but greater or lesser amounts of sieve material may be equivalently used. Consider for purposes of explanation sieve bed 14, with the understanding that the description is equally applicable to sieve bed 16. Atmospheric air is forced through the sieve bed 14 by compressor 10. As the air moves through the molecular sieve material, the nitrogen flow is impeded while oxygen and argon move through less impeded. The gas stream exiting the sieve bed 14 has increased oxygen content (e.g., 90% oxygen content or greater), and may be referred to as enriched gas or as an enriched gas stream. Forcing atmospheric air into to the sieve bed may also be referred to as "filling" the sieve bed, and the period of time when air is forced through may be referred to as the "fill cycle."

However, atmospheric air cannot be forced through the sieve bed 14 indefinitely as the bed eventually becomes loaded with nitrogen. Thus, generation of the enriched gas stream by the sieve bed 14 is periodically stopped and the nitrogen trapped in the sieve bed is purged, such as by venting the sieve bed 14 to atmosphere and/or back-flowing enriched gas. The period of time when a sieve bed is vented and/or purged maybe referred to as the "purge cycle." Considering now both the sieve beds 14 and 16, while one sieve bed generates the enriched gas stream, the second sieve bed purges, such that at least one of the sieve beds produces the enriched gas stream at any one time.

Valving system 20 controls the fill cycles and purge cycles of the sieve beds 14 and 16. Valving system 20 may take several forms. In some embodiments, valving system 20 may be a single valve having a plurality of ports to accomplish the control. In other embodiments, and as illustrated, valving system 20 comprises two valves 22 and 24. In these embodiments, each valve 22 and 24 is a solenoid operated three-port valve that selectively fluidly couples one of two ports to a common port (labled "C" in the drawings, and the arrow direction does not necessary indicate flow direction). Three-port valves 22 and 24 may be Humphrey Mini-Mizers having part number D3061A, available from John Henry Foster Company of St. Louis Mo. In the valve positions illustrated in FIG. 1, three-port valve 22 fluidly couples the compressor 10 to the sieve bed 14, and thus implements the fill cycle of sieve bed 14. Likewise, three-port valve 24 fluidly couples sieve bed 16 to an atmospheric vent, and thus implements the purge cycle of sieve bed 16. At some earlier or later time, these roles reverse, with three-port valve 22 coupling sieve bed 14 to atmospheric vent, and three-port valve 24 coupling compressor 10 to sieve bed 16.

The enriched gas stream exiting a sieve bed in the fill cycle flows through a check valve 28, and then to the product tank 26. Likewise, when sieve bed 16 is in the fill cycle, the enriched gas stream passes through check valve 30 and then flows to the product tank 26. Although check valves 28 and 30, and the remaining check valves of the figure, are illustrated to be ball-check valves, any suitable check valve may be equivalently used. The check valves 28 and 30 prevent back flow from the product tank through the purging sieve bed. However, in order to assist purging, a controlled portion of the enriched gas stream is provided from the sieve bed in the fill cycle to the sieve bed in the purge cycle by way of a fluid connection through orifice 32. In accordance with at least some embodiments, the orifice 32 has an aperture diameter of approximately 30 thousandths of an inch, a length of approximately three-quarters of an inch, and allows enriched gas flow in either direction. The portion of the enriched gas stream flowing from the sieve bed in the fill cycle to the sieve bed in the purge cycle aids the purging by flushing with enriched gas. The trans-fill system 100 illustrated in FIG. 1 further comprises a purge valve 34. Much like the orifice 32, the purge valve 34 provides a portion of the enriched gas stream from the sieve bed in the fill cycle to the sieve bed in the purge cycle, but in accordance with embodiments of the invention the purge valve 34 operates near the end of the purge cycle to "pre-charge" the sieve bed with enriched gas for the next fill cycle. The time of use of the purge valve 34 is discussed below with respect to FIGS. 2A and 2B. In accordance with some embodiments, the purge valve is a two-port solenoid operated valve, such as Humphrey two-port valves having part number D2048 available from the John Henry Foster Company.

In at least some embodiments, compressor 10 generates a compressed air stream having a pressure from approximately 20 PSI to approximately 35 PSI. Thus, the enriched gas stream accumulates in the product tank with a pressure of approximately 20 PSI to 35 PSI. However, in order to fill a portable cylinder, such as cylinder 36, the pressure of the enriched gas stream needs to be increased. In order to increase the pressure of the enriched gas stream, the trans-fill system 1000 further comprises the intensifier 18. The intensifier 18 fluidly couples to the product tank 26 through valve 68. The purpose and operation of valve 68 is discussed more below. The intensifier increases the pressure of the enriched gas stream to a pressure sufficient to fill a cylinder. For example, if the "full" pressure of cylinder 36 is 2200 PSI, the intensifier 18 generates a peak pressure at its outlet 40 of approximately 2700 PSI. Other "full" pressures and peak pressures may be equivalently used.

The term "intensifier" in this specification and in the claims refers to a class of compressor devices that compresses in stages using pistons, and where the motive force for the compression is also supplied by a piston. Thus, the illustrative intensifier 18 has a first stage 42 comprising a piston and cylinder, and also has second stage 44 comprising a piston and cylinder. The first stage 42 and the second stage 44 form the compression or compressive portion of the intensifier. The motive force for the compression comes from a motive portion 46 comprising a piston and cylinder coupled to the first stage 42 and the second stage 44 by way of a shaft 48. In the orientation of FIG. 1, as the first stage 42 piston shuttles right, the piston draws low pressure enriched gas from the product tank 26. The motive portion 46 then forces second stage 44 piston to shuttle left, which compresses the enriched gas in the first stage 42 and draws the partially compressed enriched gas to the second stage 44. As the second stage 44 compresses the enriched gas to produce a high pressure enriched gas supplied to the cylinder 36 through a cylinder fill connector 48, the first stage again draws enriched gas from the product tank 26. The intensifier 18 may be a part number 200336-1 intensifier produced through Chad Therapeutics, Inc., of Chatsworth Calif.

As illustrated in FIG. 1, the motive portion 46 of the intensifier 18 is preferably driven by compressed air supplied by the compressor 10. Valving system 50 controls the shuttling of the intensifier 18, and may take several forms. In some embodiments, valving system 50 may be a single valve having a plurality of ports to appropriately apply the compressed air to accomplish the shuttling of the intensifier. In other embodiments, and as illustrated, valving system 50 comprises two valves 52 and 54. In these embodiments, each valve 52 and 54 is a solenoid operated three-port valve that selectively fluidly couples one of two ports to a common port (labeled "C" in the drawings, and the arrow does not necessarily indicate flow direction). Like three-port valves 22 and 24, three-port valves 52 and 54 may be Humphrey Mini-Mizers available from John Henry Foster Company. In the valve positions illustrated in FIG. 1, three-port valve 52 fluidly couples the compressor 10 to motive portion 46 to perform the high pressure stroke of the second stage 44, and simultaneously valve 54 vents its side of the motive portion 46. Thereafter, three-port valve 54 fluidly couples the compressor 10 to motive portion 46 to perform the low pressure stroke of the first stage 42, and simultaneously three-port valve 54 vents its side of the motive portion 46. In some embodiments, the shuttling of the intensifier 18 is coordinated to the fill cycle and purge cycle of the sieve beds 14 and 16.

Trans-fill system 1000 in accordance with embodiments of the invention also comprises a processor 56. The processor 56 may be a microcontroller, and therefore the microcontroller may be integral with read only memory (ROM) 58, random access memory (RAM) 60, a digital output (DO) module 62 and an analog-to-digital (A/D) converter 66. In alternative embodiments the processor 56 may be implemented as a standalone central processing unit in combination with individual ROM, RAM, DO and A/D devices.

The ROM 58 stores instructions executable by the processor 54. In particular, the ROM 58 comprises software programs that coordinate control of the sieve beds and intensifier by controlling the various two-port and three-port valves in the trans-fill system 1000. The RAM 60 is the working memory for the processor 56, where data is temporarily stored, and from which instructions are executed. Processor 54 couples to other devices within the trans-fill system by way of the digital output module 62 and A/D module 66. In particular, the processor 54 electrically couples to and controls three-port valves 22 and 24 of the valving system 20, and valves 52 and 54 of the valving system 50, by way of digital output module 62. Processor 56 also electrically couples and controls three-port valve 68, as well as two-port valves 34 and 70, by way of the digital output module 62. Finally with respect to the digital output module 62, the processor couples to and implements on/off control off the compressor 10.

A trans-fill system 1000 in accordance with at least some embodiments of the invention also has a plurality of analog signals of interest within the system, and thus the processor couples to devices creating analog signals by way of the A/D converter 66. In particular, processor 56 may couple to a pressure transducer 72 and a gas analyzer 74 by way of the A/D converter. Gas analyzer 74 fluidly couples to and samples the enriched gas stream as it exits the product tank 26, but the enriched gas stream may be equivalently sampled at other locations as well. The gas analyzer 74 determines the oxygen content of the enriched gas. The gas analyzer 74 may be, for example, an oxygen-selective sensor such sensors based on zirconium oxide, galvanic, or paramagnetic technologies. In accordance with embodiments of the invention, if on start-up of the trans-fill system the oxygen content of the enriched gas stream is below a predetermined threshold (e.g. 90% oxygen), or during operation the oxygen content falls below the predetermined threshold, then the enriched gas stream is preferably not provided to cylinder 36.

At initial start-up of the trans-fill system 1000, it may take several fill cycles and purge cycles of the sieve beds 14 and 16 before the enriched gas stream meets or exceeds the predetermined threshold of oxygen concentration. In some configurations, the sieve beds 14 and 16 may need to be operational for three to five minutes before the enriched gas meets or exceeds the threshold. Likewise during operation, when the oxygen content drops, the sieve beds 14 and 16 may need to be operational for several fill cycles and purge cycles before the enriched gas oxygen content again meets or exceeds the predetermined threshold. In order not to provide the enriched gas below the predetermined threshold to the cylinder 36, when the enriched gas oxygen content falls below the predetermined threshold, the enriched gas stream is blocked from the intensifier 18 by way of valve 68 under control of the processor 56. However, there are several considerations when ceasing the enriched gas flow, such as what to do with the substandard enriched gas stream, and how to handle operation of the intensifier 18 when the enriched gas stream is blocked. The latter is addressed first.

Still referring to FIG. 1, illustrative trans-fill system 1000 uses compressor 10 to supply compressed air both the sieve beds 14 and 16, and as the driving force of the motive portion 46 of the intensifier 18. Thus, compressor 10 has sufficient capacity to supply both the sieve beds and the intensifier; however, if the compressed air produced is not consumed, the compressor 10 tends to over-pressure, which may cause activation of pressure relief valves of the compressor 10. In order to avoid this situation, and in accordance with embodiments of the invention, the intensifier 18 continues to operate even in the absence of the enriched gas stream being provided to the intensifier. Stated otherwise, the motive portion 46 of the intensifier continues to draw compressed air from the compressor 10 when the valve 68 blocks flow of enriched gas from the product tank.

The other consideration when ceasing enriched gas flow to the intensifier 18 is that the sieve beds 14 and 16 still need to generate the enriched, though substandard, gas stream so that the oxygen concentration can be improved. Thus, enriched gas in the product tank needs to be released. Releasing the enriched gas from product tank 26 may take many forms. In some embodiments, the product tank 26 continuously releases a portion of the enriched gas, such as through orifice 76. In these embodiments, a portion of the enriched gas is released from the product tank at all times. In these embodiments where gas is released from the product tank 26 continuously, the orifice 76 may be selected or adjusted to release approximately 0.5 liters per minute.

Rather than release enriched gas at all times, alternative embodiments utilize the dump valve 70 and orifice 78. In these embodiments, when the intensifier 18 is not provided the enriched gas stream, the dump valve 70, under control of the processor 56, is opened to release the substandard enriched gas from the product tank 26. At times when the oxygen content of the enriched gas is above the predetermined threshold, the dump valve 70 closes and valve 68 (in these embodiments operated as a two-port on-off valve, though not specifically illustrated as such) allows the enriched gas stream to flow to the intensifier. In accordance with the embodiments using dump valve 70, the orifice 78 may be selected or adjusted to release approximately 2 liter per minute.

Rather than selectively release enriched gas through dump valve 70, or continuously release enriched gas through orifice 76, yet still further alternative embodiments use three-port valve 68 coupled between the product tank 26 and the intensifier 18 for this purpose. In a first valve position, the three-port valve supplies the enriched gas stream to the intensifier 18; however, when the oxygen content of the enriched gas stream drops below the predetermined threshold, the valve 68, under control of the processor 56, changes position and releases the substandard enriched gas through orifice 80. In these embodiments, the orifice 80 may be selected or adjusted to release approximately 2 liters per minute.

Still referring to FIG. 1, regardless of the precise embodiments used to release enriched gas from the product tank, at least some embodiments release the gas inside the case of the trans-fill system 1000. More particularly, in at least some embodiments the released enriched gas flows through tubing 64 that terminates proximate to the air inlet 12 of the compressor (e.g., within approximately three inches). In embodiments where the compressor 10 comprises an inlet filter, the enriched gas may be released anywhere inside the housing of the inlet filter. In this way, the enriched gas released is, in whole or in part, drawn in by the compressor 10. Re-compressing the substandard but otherwise enriched gas, and providing that gas to the sieve beds 14 and 16, may shorten the amount of time it takes the sieve beds to reach a state where the enriched gas stream is of sufficient oxygen content, or shorten recovery time when oxygen content falls below the predetermined threshold. In yet still further alternative embodiments, the enriched gas released by any of the mechanisms discussed above may couple to a port accessible through an aperture in the case. Using this port, a home care provider or other interested person may independently verify the oxygen content using a separate gas analyzer. In embodiments that release the enriched gas using the dump valve 70 or the valve 68, the home care provider or interested person may force a release even when the gas analyzer 74 of the trans-fill system 1000 shows the oxygen content to be above the predetermined threshold and the intensifier is supplied the enriched gas. For example, the home care provider or other interested person may force release by way of the user interface 82.

The discussion now turns to coordination of control of the various components of the trans-fill system 1000. For purposes of this discussion it is assumed that the valving system 20 comprises two separate valves (and thus two independent control signals). Likewise, it is assumed that the valving system 50 comprises two separate valves (and thus two independent control signals). Further, for purposes of this discussion, "on" or "asserted" states of control signals are illustrated as high voltage, and "off" or "de-asserted" states of control signals are illustrated as low voltage; however, the assignment of asserted states to voltage levels is merely exemplary, and "asserted" in practice may equivalently be a low voltage state. Moreover, particular actions discussed as performed in an asserted state may be equivalently performed in a de-asserted state.

FIG. 2A illustrates a timing diagram for control of various components of the trans-fill system 1000. During time frame 200, the control signal 202 applied to the control valve 22 for sieve bed 14 is asserted, indicating that sieve bed 14 is in the fill cycle. Likewise during time frame 200, control signal 204 applied to the control valve 24 for sieve bed 16 is de-asserted, indicated that sieve bed B is in the purge cycle. After a certain amount of time, in some embodiments approximately six seconds, the control signal 202 becomes de-asserted while control signal 204 becomes asserted. Thus, in time frame 206 sieve bed 14 is in the purge cycle while sieve bed 16 is in the fill cycle. The pattern of alternate fill cycle and purge cycle continues during operation of the oxygen concentrator.

FIG. 2A further illustrates control signals 208 and 210 that couple to control valves 52 and 54, respectively. Control valves 52 and 54 control the low pressure and high pressure stroke, respectively, of the motive portion 46 of the intensifier 18. Thus, when control signal 210 is asserted, the motive portion 46 of the intensifier 18 performs the low pressure stroke, and when control signal 208 is asserted, the motive portion 46 of the intensifier 18 performs the high pressure stroke. As illustrated in FIG. 2A, and in accordance with embodiments of the invention, there is at least one low pressure stroke and one high pressure stroke during a fill cycle/purge cycle (hereinafter, just cycle) of a sieve bed. More particularly, FIG. 2A illustrates embodiments where there are three strokes of motive portion 46 during each cycle. Time frame 200 illustrates two low pressure strokes and one high pressure stroke, while the contiguous time frame 206 illustrates two high pressure strokes and one low pressure stroke. Having three strokes of the motive portion 46 during each cycle is a function of the volume of sieve beds, the capacity of the compressor 10 and the capacity of the intensifier 18. Holding the capacity of the compressor 10 and intensifier 18 constant, increasing the volume of sieve beds increases the possible fill time and therefore the number of strokes of the motive portion 46 possible during a cycle. Decreasing the volume of sieve beds decreases the possible fill time and therefore the number of strokes possible. Holding the amount of sieve material constant, increasing the capabilities of the compressor 10 and/or intensifier 18 decreases the possible fill time and therefore the number of strokes of the motive portion 46 during the cycle. Decreasing the capabilities of the compressor 10 and/or intensifier 18 increases the possible fill time and therefore the number of strokes possible.

FIG. 2A further illustrates control signal 212 that couples to purge valve 34. When control signal 212 is asserted, the purge valve 34 allows flow of enriched gas between the sieve beds. In accordance with embodiments of the invention, while enriched gas flows between the sieve beds at all times by way of orifice 32, just after the end of a purge cycle of a sieve bed the purge valve 34 is activated to "pre-charge" the purged sieve bed with enriched gas from the sieve bed that just completed the fill cycle. Time frame 200 shows operation of the purge valve by illustrative pulse 214. Likewise, time frame 206 shows operation of the purge valve by illustrative pulse 216. In accordance with at least some embodiments of the invention the purge valve is active for approximately 100 to 400 milli-seconds. In accordance with at least some embodiments, both the control signals 202 and 204 for the sieve beds are de-asserted during the period of time that the control signal 212 for the purge valve is asserted; however, the granularity of the time scale of the illustrative timing diagrams is so large that these features are not visible. With respect to cycles where a low pressure stroke is the last stroke of the cycle, in some embodiments the low pressure stroke ends substantially simultaneously with the end of the fill cycle and the high pressure stroke starts substantially simultaneously end of the fill cycle. With respect to cycles where a high pressure stroke is the last stroke of the cycle, in some embodiments the high pressure stroke continues after the end of the fill cycle to include the time that the purge valve control signal 212 is asserted. At the end of the purge time, both the high pressure stroke control signal 210 and the purge valve control signal 212 are de-asserted, while the low pressure stroke control signal 208 is asserted.

FIG. 2B, plotted on a corresponding "X" or time axis, but on a different "Y" axis, shows an illustrative gas analyzer output signal 218 as function of time, and also shows control signal 220 that couples to the control valve 68 and control signal 222 that couples to the dump valve 70. In embodiments where the control valve 68 is a three-port valve, when control signal 220 is asserted, control valve 68 fluidly couples the intensifier 18 to the sieve beds and/or product tank. When control signal 220 is de-asserted, the control valve 68 releases enriched gas from the product tank through orifice 80. Dashed line 224 illustrates a point in time where the oxygen concentration of the enriched gas reaches a predetermined threshold (e.g., 90% oxygen concentration). When the predetermined threshold is reached, the control signal 220 coupled to the control valve 68 is asserted, thus fluidly coupling the intensifier 18 to the enriched gas stream. FIG. 2B also illustrates, by dashed line 226, a point in time where the oxygen concentration falls below the predetermined threshold. In this situation, the control signal 220 coupled to the control valve 68 is de-asserted, thus de-coupling the intensifier 18 from the enriched gas stream and releasing enriched gas through orifice 80.

In alternative embodiment where control valve 68 is operated as a two-port valve and the dump valve 70 is used, when the predetermined threshold oxygen concentration is reached (again at the time illustrated by dashed line 224), the control signal 222 coupled to the dump valve 78 is de-asserted, thus ceasing the release of the enriched gas from the product tank. Simultaneously, the control signal 220 coupled to the control valve 68 is asserted, thus fluidly coupling the enriched gas to the intensifier 18. When the oxygen concentration falls below the predetermined threshold (again at the time illustrated by dashed line 226), the control signal 222 coupled to the control valve 70 is asserted, thus releasing enriched gas through orifice 78. Simultaneously, the control signal 220 coupled to the control valve 68 is de-asserted, thus blocking the flow of enriched gas stream to the intensifier.

Returning now to FIG. 1, trans-fill system 1000 comprises a pressure transducer 72 fluidly coupled to the cylinder 36 downstream of fill orifice 41. In accordance with at least some embodiments, pressure transducer 72 may be a part number MLH03KPSP01A pressure transducer available from Honeywell of Morris Township N.J. Unlike pressure switches, which open or close an electrical contact at a predetermined pressure, a pressure transducer may provide a substantially continuous reading of pressure. The pressure transducer 72 in accordance with at least some embodiments assists the processor 56 in performing several functions. Firstly, the pressure transducer 72 senses the pressure of enriched gas within cylinder 36, and when the average pressure reading of the cylinder 36 reaches the "full" pressure (e.g., 2200 PSI), the processor 56 turns off the trans-fill system by turning off the compressor 10.

The second function that the processor 56 performs with the pressure reading provided by the pressure transducer 72 is adjusting the time for the high pressure stroke of the motive portion 46 of the intensifier 18. In particular, when the cylinder 36 is only partially filled (e.g., having a bottle pressure less than approximately 1200 PSI), the "dead-head" pressure against which the second stage 44 of the intensifier 18 must work is relatively low. In these situations, the high pressure stroke of motive portion 46 may take about the same amount of time as the low pressure stroke. In some embodiments, a fill cycle of a sieve bed is approximately six seconds, and with three strokes per cycle, each stroke takes approximately two seconds. However, as the pressure within the bottle rises (e.g., above 1200 PSI up to the "full" pressure of 2200 PSI), the dead-head pressure against which the second stage 44 works means that it may take more time to complete the high pressure stroke. In accordance with at least some embodiments of the invention, the processor 56 monitors the pressure provided by the pressure transducer 72, and adjusts the time for the high pressure stroke of the intensifier 18 based on the pressure. In response, time for the fill cycle of the sieve bed may be correspondingly increased. For example, in the illustrative embodiments discussed, as the pressure in the bottle increases the time for high pressure stroke may be increased from two seconds to two and a half seconds. In cycles where there is only one high pressure stroke, the cycle time may be increased from six seconds to six and a half seconds. Where there are two high pressure strokes, the cycle time may be increased to seven seconds. In yet still further embodiments, the time to complete the high pressure stroke may be directly proportional to the bottle pressure. For example, as bottle pressure increase from 1200 PSI to 2200 PSI, the high pressure stroke time may be correspondingly and incrementally increased from two seconds to two and a half seconds.

In yet still further alternative embodiments, the time allotted to the high pressure stroke may be adjusted based on other factors, such as the available pressure for the high pressure stroke from the compressor 10. In particular, at times when the compressed air pressure from the compressor 10 is low (e.g., the very early portions of a fill cycle of a sieve bed), the time for the high pressure stroke may be increased to compensate for the lower motive pressure. These time increases may be independent of the pressure of cylinder 36. At least some embodiments attempt to lessen the effect of reduced pressure during the very early portions of the fill cycle by implementing an amount of time where neither sieve bed draws air from the compressor, thus allowing the compressor time to increase just prior to beginning the next fill cycle. The amount of time where neither sieve bed draws air from the compressor may be on the order of approximately 100 milliseconds. Allowing the compressor time to build pressure may also decrease an amount of time needed to complete the high pressure stroke of the intensifier, and thus may delay the time when the high pressure stroke time is increased.

In addition to adjusting the time for the high pressure stroke and turning off the compressor 10 as a function of the pressure of the cylinder 36, the processor 56 may perform other useful functions based on the pressure read by the pressure transducer 72. For example, when the rate of pressure increase is very significant (e.g. the average pressure arising several hundred PSI in a single high pressure stroke), this may indicate a bad connection between the cylinder 36 and the fill connector 48. Likewise, if the rate of pressure increase falls to zero, yet the average pressure is below the expected "full" pressure, the trans-filled device 1000 is most likely being operated at high altitudes and no further pressure is possible. In these situations, the processor 56 may stop the compressor 10, and therefore filling of the cylinder 36, as no further pressure may be achievable. Relatedly, if a cylinder 36 has been filled but is left coupled to the trans-fill device 1000, it may over time lose pressure. In accordance with at least some embodiments, when the pressure leaks off to be below a certain predetermined threshold, the processor 56 may restart the compressor 10 and re-fill cylinder 36 to the "full" level.

Figure 3:
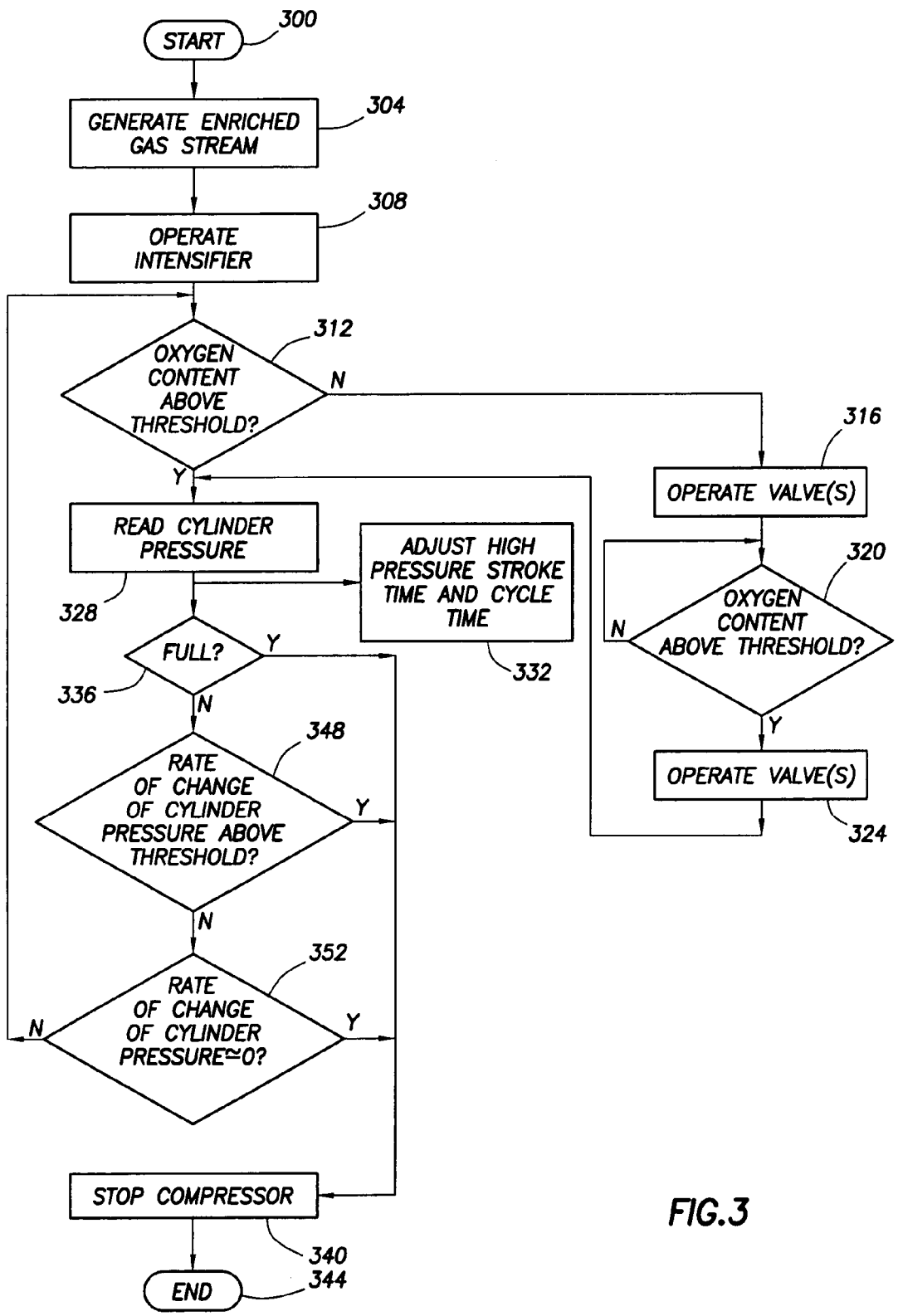
FIG. 3 illustrates a flow diagram in accordance with the embodiments of the invention.

FIG. 3 illustrates a method in accordance with a embodiments of the invention. In particular, the method may start (block 300) by a user placing a cylinder 36 in a cylinder fill connector 49. Thereafter, the trans-fill system generates an enriched gas stream (block 304). Additionally, the intensifier is operated (block 308). The enriched gas stream is tested to determine if the oxygen content is above a predetermined threshold (block 312). If the trans-fill system 1000 has been in a non-operational state for an extended period of time, initially the oxygen content of the enriched gas stream will be below the predetermined threshold. Therefore the trans-fill system operates one or more valves (block 316) to refrain from providing the enriched gas stream to the intensifier. In some embodiments, only valve 68 between the products tank 26 and the intensifier 18 is operated, blocking the flow to the intensifier and also releasing therapeutic gas through orifice 80. In alternative embodiments, valve 68 acts only to block the flow of the enriched gas stream to the intensifier, and additionally dump valve 70 is operated to allow release of enriched gas to orifice 78. In yet further embodiments, valve 68 operates only to block the flow enriched gas from the product tank 26 to the intensifier 18, and the substandard enriched gas accumulated in the product tank is released through orifice 76.

Regardless of the precise mechanisms that operates to refrain from providing the enriched gas stream to the intensifier and releasing enriched gas from the product tank, the next step is yet another determination of whether the oxygen content of the enriched gas stream is above the predetermined threshold (block 320). If not, the program loops at this step until the oxygen content of the enriched gas stream rises above the predetermined threshold. In this instance, the one or more valves are operated (block 324). In embodiments where enriched gas is released by operation of a valve, those valves are operated to cease the release of enriched gas and other valves (or possibly the same valve) are operated to provide the enriched gas stream to the intensifier 18.

Still referring to FIG. 3, thereafter, the cylinder pressure is read (block 328), and the program or method takes two parallel paths. On the first path, and in some embodiments, the processor 56 adjusts the high pressure stroke time, and possibly the cycle time, as a function of the cylinder pressure (block 336). The second path is a determination of whether the cylinder is full (block 336). If the cylinder is full, the process jumps immediately to stopping the compressor (block 340) and the process ends (block 344). If, on the other hand, the cylinder is not full (again block 336), the next step may be determining if the rate of change of cylinder pressure is above the predetermined threshold (block 348). As discussed above, if the rate of change of the cylinder pressure is above a predetermined threshold, this may indicate that the cylinder 36 is not properly coupled to the cylinder fill connector 49, and the only thing being filled is the tubing between the intensifier 18 and the cylinder fill connector 49. If the rate of change is above the predetermined threshold, the compressor is stopped (block 340), and again the process ends (block 344). If, on the other hand, the rate of change is below the predetermined threshold, the next step is a determination whether the rate of change in cylinder pressure approximately zero (block 352). If the rate of change in cylinder pressure is approximately zero, this may indicate that the trans-fill system is being operated at high altitudes and may not be able to reach the "full" pressure of the cylinder, therefore, the compressor is stopped (block 340), and the process ends (block 344). If, on the other hand, the rate of change of cylinder pressure is greater than zero, then process retreats to determining whether the oxygen content is above the predetermined threshold (again block 312).

Using the amount and type of sieve material noted, the compressor and intensifier noted, and the various control strategies noted, a trans-fill system 1000 in accordance with embodiments of the invention should be capable of filling a cylinder at or greater than 2 liters per minute when the cylinder pressure is less than approximately 1200 PSI. Further, the trans-fill system 1000 should be capable of filling the cylinder at approximately 1.75 to 2.0 liters per minute when the cylinder pressure is above approximately 1200 PSI.

The above discussion is meant to be illustrative of the principles and various embodiments of the present invention. Numerous variations and modifications will become apparent to those skilled in the art once the above disclosure is fully appreciated. For example, many of the control signals illustrated in FIGS. 2A and 2B are merely logical NOTs of each other. Thus, a trans-fill system need not have separate digital outputs for each of these signals; instead, one digital output may be used the control signal logically noted to produce the second signal, or the controlled valve may be selected to activate on an opposite asserted state. This specification discusses cylinders having "full" pressure at approximately 2200 PSI; however, other "full" pressures, both higher and lower, may be equivalently used. Further, while the various embodiments are described as implemented in part by a processor 56, the various controls strategies could be equivalently implemented by way of a hardware state machine, and in some cases pneumatically (particularly the valve control strategies). It is intended that the following claims be interpreted to embrace all such variations and modifications.

What is claimed is:

1. A method comprising:
   generating an enriched gas stream from atmospheric air;
   operating an intensifier which, when provided the enriched gas stream, produces a cylinder fill gas stream, and wherein the operating continues in the absence of the enriched gas stream being provided to the intensifier.

2. The method as defined in claim 1 further comprising:
   analyzing oxygen content of the enriched gas stream; and
   refraining from providing the enriched gas stream to the intensifier when the oxygen content is below a predetermined threshold.

3. The method as defined in claim 2 further comprising supplying the cylinder fill gas stream to a cylinder when the oxygen content is above the predetermined threshold.

4. The method as defined in claim 2 further comprising releasing at least a portion of the enriched gas stream when the oxygen content is below the predetermined threshold.

5. The method as defined in claim 4 wherein releasing further comprises releasing proximate to an inlet of a compressor that supplies air to a device that generates the enriched gas stream.

6. The method as defined in claim 2 wherein refraining further comprises refraining from providing when the oxygen content is below approximately 90 percent.

7. The method as defined in claim 1 further comprising continuously releasing a portion of the enriched gas stream.

8. The method as defined in claim 7 wherein continuously releasing further comprises continuously releasing approximately 0.5 liters per minute.

9. The method as defined in claim 7 wherein continuously releasing further comprises releasing proximate to an inlet of a compressor that supplies air to a device that generates the enriched gas stream.

10. The method as defined in claim 1 further comprising sensing attributes of the cylinder fill gas stream with a pressure transducer.

11. The method as defined in claim 10 further comprising ceasing generating and operation if one or more selected from the group: the rate of pressure increase of the portable gas cylinder is substantially zero yet below a predetermined full threshold; and the rate of pressure increase indicated incomplete coupling to the portable gas cylinder.

12. A system comprising:
    a compressor;
    a concentrator fluidly coupled to the compressor, the concentrator creates an enriched gas stream;
    an intensifier with a motive portion and a compression portion, the motive portion fluidly coupled to the compressor, and the compression portion fluidly coupled to the enriched gas stream on one side and configured to couple to a portable gas cylinder on a second side, wherein the compression portion compresses the enriched gas stream to create a high pressure enriched gas stream; and
    a control valve fluidly coupled between the concentrator and the intensifier, the valve selectively blocks enriched gas flow to the intensifier;
    wherein the motive portion of the intensifier continues to draw compressed air from the compressor when the control valve blocks enriched gas flow to the compression portion of the intensifier.

13. The system as defined in claim 12 further comprising:
    a gas analyzer fluidly coupled to the enriched gas stream;

a processor electrically coupled to the gas analyzer and an actuator of the control valve;

wherein the processor commands the control valve to block enriched gas flow to the intensifier when an oxygen content of the enriched gas stream is below a predetermined threshold.

14. The system as defined in claim 13 wherein the predetermined value is 90% oxygen concentration.

15. The system as defined in claim 13 further comprising:
a dump valve fluidly coupled to the enriched gas stream which selectively releases enriched gas;

wherein the processor commands the dump valve to release enriched gas when the oxygen content of the enriched gas stream is below the predetermined threshold.

16. The system as defined in claim 15 further comprising a tubing fluidly coupled to the dump valve on a first end, and a second end of the tubing proximate to an inlet of the compressor.

17. The system as defined in claim 15 wherein when the dump valve releases enriched gas at approximately 2 liter per minute.

18. The system as defined in claim 15 wherein the control valve and the dump valve are the same valve.

19. The system as defined in claim 18 wherein the dump valve releases enriched gas at a flow of approximately 2 liters per minute.

20. The system as defined in claim 12 further comprising a port that allows continuous controlled release of a portion of enriched gas stream.

21. The system as defined in claim 20 wherein the portion of the enriched gas stream escapes through the port at approximately 0.5 liters per minute.

22. The system as defined in claim 20 further comprising:
a case, wherein at least one of the compressor, PSA system, product tank, intensifier or control valve are within the case;

wherein the port is exposed through an aperture of the case, and the port is configured to couple to a portable gas analysis device.

23. The system as defined in claim 12 wherein the control valve further couples to a valve position controller electrically coupled to the processor, wherein the processor selectively controls the flow rate through the valve.

24. The system as defined in claim 12 further comprising:
a pressure transducer fluidly coupled to the high pressure enriched gas stream;

a processor electrically coupled to the pressure transducer, wherein the processor detects attributes of filling the portable gas cylinder.

25. The system as defined in claim 24 wherein the processor performs one or more selected from the group: turns off the compressor if the rate of pressure increase in the portable gas cylinder is substantially zero yet below a first predetermined threshold pressure; turns off the compressor if the rate of pressure increase indicates an inadequate coupling of the portable gas cylinder to the intensifier; and restarts the compressor if the pressure the portable gas cylinder leaks off to below a second predetermined threshold pressure.

* * * * *